United States Patent [19]
Kambara

[11] Patent Number: 6,054,035
[45] Date of Patent: Apr. 25, 2000

[54] DNA SAMPLE PREPARATION AND ELECTROPHORESIS ANALYSIS APPARATUS

[75] Inventor: Hideki Kambara, Hachioji, Japan

[73] Assignee: Hitachi, Ltd., Tokyo, Japan

[21] Appl. No.: 08/897,833

[22] Filed: Jul. 21, 1997

[30] Foreign Application Priority Data

Jul. 24, 1996 [JP] Japan .................................. 8-194341

[51] Int. Cl.[7] ................................................. G01N 27/26
[52] U.S. Cl. ...................................................... 204/601
[58] Field of Search ............................ 435/287.2, 288.4; 204/451, 450, 601, 600, 453, 604

[56] References Cited

U.S. PATENT DOCUMENTS

| | | | |
|---|---|---|---|
| 4,806,316 | 2/1989 | Johnson et al. ........................ | 422/100 |
| 4,908,112 | 3/1990 | Pace ....................................... | 204/98.2 |
| 5,194,133 | 3/1993 | Clark et al. ............................. | 204/608 |
| 5,585,069 | 12/1996 | Zanzucchi et al. ..................... | 422/100 |
| 5,624,800 | 4/1997 | Grossman et al. ..................... | 435/6 |
| 5,630,925 | 5/1997 | Pentoney, Jr. et al. ................ | 204/604 |
| 5,648,213 | 7/1997 | Reddy et al. ........................... | 435/6 |
| 5,661,028 | 8/1997 | Foote ..................................... | 435/287.2 |

FOREIGN PATENT DOCUMENTS

776700 A1   6/1997   European Pat. Off. .

*Primary Examiner*—Jill Warden
*Assistant Examiner*—Alex Noguerola
*Attorney, Agent, or Firm*—Antonelli, Terry, Stout & Kraus, LLP

[57] ABSTRACT

The DNA sample preparation apparatus of the present invention comprises a base plate having a plurality of first grooves for fixing two or more kinds of DNA samples or primers to the inner surfaces of the grooves, respectively, a second groove communicating with the plurality of the first grooves, wherein a reaction solution is introduced into the first grooves to be reacted with the two or more kinds of said DNA samples or primers independently at the same time.

2 Claims, 6 Drawing Sheets

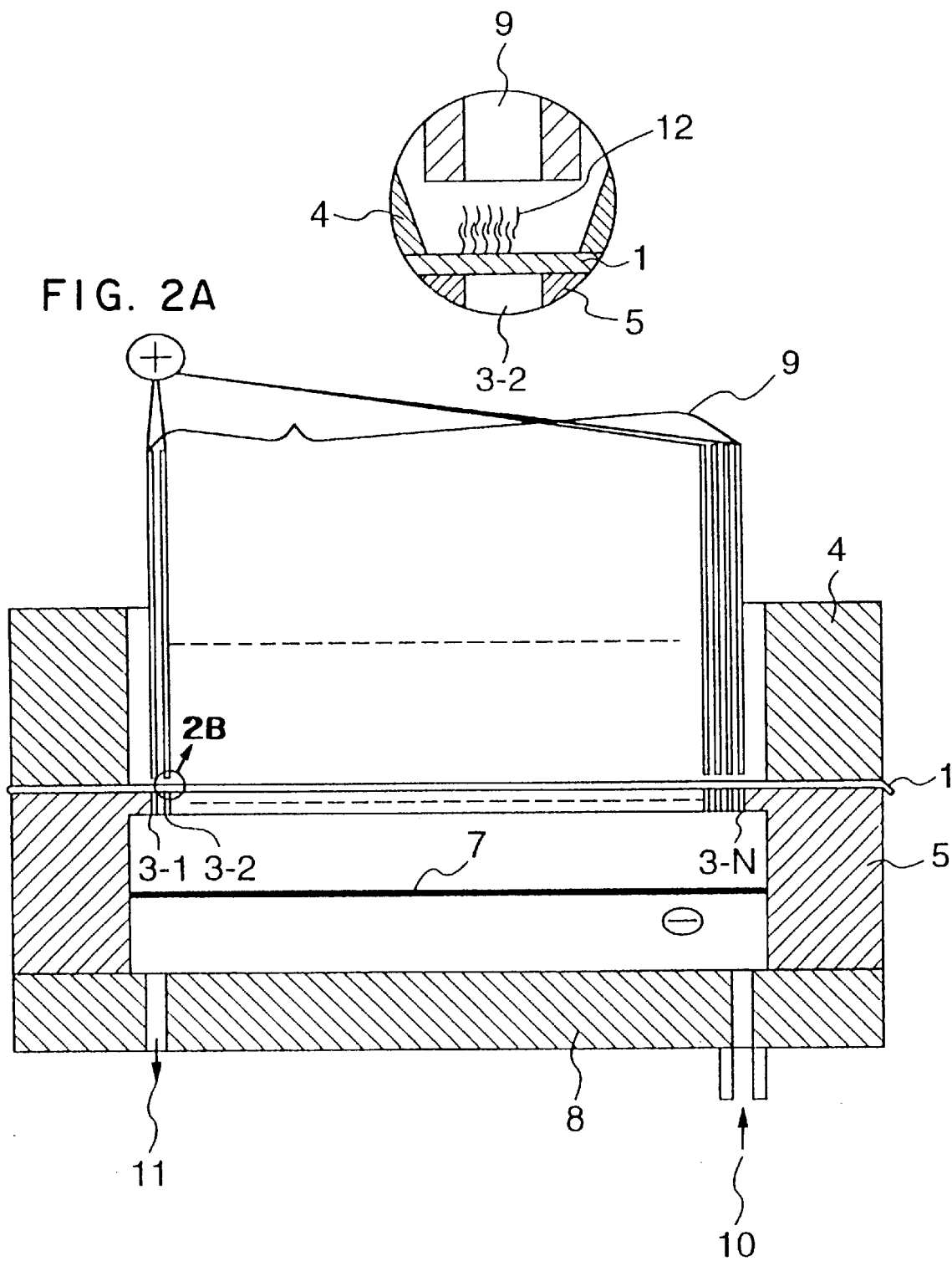

B-B' CROSS SECTION

FIG.5A
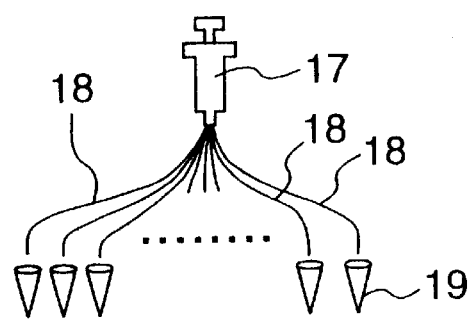
FIG.5B
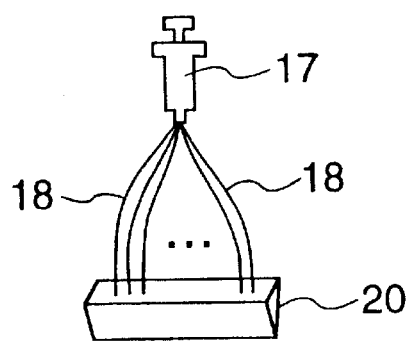
FIG.5C
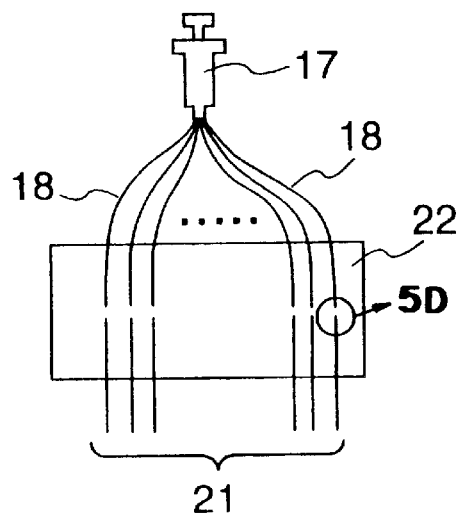
FIG. 5D
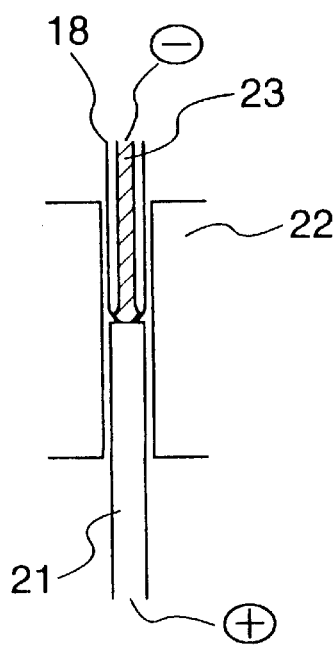

DNA SAMPLE PREPARATION AND ELECTROPHORESIS ANALYSIS APPARATUS

BACKGROUND OF THE INVENTION

1. Field of the Invention

The present invention relates to a method for analysis of DNA and the like using capillary array electrophoresis and an apparatus for the analysis.

2. Description of the Related Art

Capillary gel electrophoresis is a rapid and highly sensitive analysis method and is noted as a promising method particularly for DNA analysis including DNA base sequence determination (DNA sequencing). In addition, a capillary array apparatus composed of capillary analyzing tubes put side by side has been developed for increasing the analyzing through-put by analyzing a large number of samples in parallel. In such apparatus, samples are held in a titer plate or a sample bottle, electrodes and the ends of capillaries are put into the titer plate or the sample bottle, and the samples are electrically introduced into the capillaries by application of an electric field between the electrodes and the ends of the capillaries.

On the other hand, there is a growing demand for DNA analysis such as DNA sequencing with the progress of Human Genome Project, and the development of an efficient DNA analysis method is desired. A DNA sequencer using a capillary array gel electrophoresis is also a promising apparatus for the DNA analysis. In addition to such an analyzing apparatus, the improvement of the efficiency of sample preparation and injection into the analyzer has become necessary and various pipetting apparatus are on the market. For preparing samples for DNA sequencing or the like, there is usually used a tube having a capacity of 0.5 ml or a 96-well titer plate. Titer plates are suitable for preparing a large number of samples and are widely used. As to the total volume of reagents used in the reactions carried out in the titer plate, the reaction volume is about 10 $\mu$l and cannot be reduced because of the reaction efficiency, and titer plates with a capacity of approximately 100–200 $\mu$l are widely used. Substantially the whole amount of the reaction products obtained by the use of a titer plate are used for measurement in a DNA sequencer commercialized with a slab gel, but the amount of samples used in a DNA sequencer using capillaries is one hundredth or less as large as the amount of samples used for measurement using the slab gel. This means that there is a great possibility to reduce the amount, therefore the cost, of reagent(s) used in DNA analysis. However, the conventional sequencing reaction procedure is not suitable for this purpose.

Thus, a new tool or method is needed wherein a small amount of reagent is consumed and a small amount of products are efficiently introduced into the capillaries.

SUMMARY OF THE INVENTION

An object of the present invention is to provide a DNA sample preparation apparatus which permits reduction of the amount of reagents used, cost reduction and reduction of the number of reactions for labor saving; a method for analyzing DNA or the like by using capillaries array electrophoresis in which large-scale base sequence analysis is carried out by the use of prepared DNA samples; and an apparatus for the analysis.

The present invention provides a sample preparation apparatus suitable for a capillary array type electrophoresis apparatus in which the amount of samples consumed is small. In detail, by the use of a vessel having therein a plurality of separate sample preparation reaction areas, a series of different reactions are carried out in a solution in different places, and the reaction products are held near these places. The samples prepared in the sections (the sample preparation reaction areas) are introduced into different capillaries, respectively. It is convenient to make the pitch of the capillaries at the introducing positions same as the pitch of the sections. For example, the bottom of a groove as vessel is composed of a filter-like membrane permeable to water, buffer, etc. (e.g. filter paper or glass filter), avidin is immobilized on the surface of the filter at uniformly spaced positions, and a liquid containing template DNA tagged biotin is passed through the filter to fix the template DNA to the filter. The groove as vessel is filled with a sequencing primer and a reaction solution, and sequencing reactions are carried out. Thus, a large number of samples are prepared at the same time. The products are hybridized with the DNA fixed to the filter. The end of the capillary is brought close to the products and the products are released from the fixed DNA by heating or the like, introduced into the capillary by applying an electric field and analyzed.

In the DNA fixing portions aligned in the bottom of the groove as vessel, 10 to 20 samples can be fixed per cm when the DNA fixing portions are aligned at a pitch of 0.5 mm to 1 mm. Therefore, 50 to 100 samples can be held in a place of 5 cm width and reacted at a time. When the width of the groove is adjusted to 0.3 mm which is substantially the same as the outside diameter of the capillary, the volume of the reaction solution used is 50 mm×0.3 mm×1 mm=15 $\mu$l. Thus, 50 to 100 samples can be reacted by one operation by using the reaction solution in an amount usually required for reacting one sample. When the pitch of the DNA-holding portions is made the same as that of the capillaries of the capillaries array, samples can be introduced into the capillaries at the same time. Therefore, it is very convenient. The constitution of the present invention is explained below in further detail.

One aspect (constitution 1) of the present invention is characterized by a DNA sample preparation apparatus comprising a first component (member) for fixing two or more kinds of DNA samples or primers in its different sections, respectively, and a second component (member) having an open area, wherein reactions including DNA complementary strand syntheses are carried out at the same time and independently in the sections in a space formed by the first component (member) and the open area. More specifically, the first component (member) is composed of a filter membrane, and a biotin-tagged DNA or primer, or an antigen-tagged DNA or primer is fixed to each section of the first component (member), whereby the DNA sample or primer is fixed to the first component (member) by utilizing biotin-avidin bonding or antigen antibody reaction.

Another aspect (constitution 2) of the present invention is characterized by an electrophoresis analysis apparatus comprising a DNA sample preparation apparatus of constitution 1, an electrophoresis analyzer and at least two capillaries having a sample-introducing portion at the end in which the reaction products produced in each section of the DNA sample preparation apparatus of constitution 1 are introduced into a capillary and analyzed by electrophoresis. The analysis apparatus is characterized in that the capillaries are filled with a gel or a sol, that the disposition of the sections is substantially the same as that of the sample-introducing portions at the ends of the capillaries, and that the analysis apparatus is equipped with a means for introducing the reaction products into the sample-introducing portion at the end of the capillary.

Further another aspect (constitution 3) of the present invention is characterized by a DNA sample preparation apparatus comprising a sheet-like component (member) having a plurality of small holes formed at regular distance intervals as reaction vessels and a component (member) having an open area. A DNA sample or a primer is fixed on the inner surface of each small hole and DNA polymerase reaction is carried out; the small holes are formed of a porous material; a biotin-tagged DNA or primer, or an antigen-tagged DNA or primer is fixed in each small hole, whereby the DNA sample or primer is fixed in the small hole by utilizing biotin-avidin bonding or antigen antibody reaction; and reaction reagents are injected into a space formed by the sheet-like component (member) and a component (member) having an open area, to be fed to the small holes.

Still another aspect (constitution 4) of the present invention is characterized by an electrophoresis analysis apparatus comprising a DNA sample preparation apparatus of constitution 3, an electrophoresis analyzer and at least two capillaries having a sample-introducing portion at the end in which the reaction products produced in each small hole of the DNA sample preparation apparatus of constitution 3 are introduced into a capillary and analyzed by electrophoresis. The analysis apparatus is characterized in that the capillaries are filled with a gel or a sol, that the disposition of the small holes is substantially the same as that of the sample-introducing portions at the ends of the capillaries, and that the analysis apparatus is equipped with a means for introducing the reaction products into the sample-introducing portion at the end of the capillary.

Still another aspect (constitution 5) of the present invention is characterized by a DNA sample preparation apparatus comprising capillaries each having a DNA sample or primer fixed on the inner surface and a means for feeding a reaction solution to the capillaries, wherein DNA polymerase reactions are independently carried out inside the capillaries, respectively. This apparatus is characterized in that the number of the capillaries is two or more, that different sample DNA's are fixed in the different capillaries, that the feeding means feeds the reaction solution to the capillaries at substantially the same time, and that a biotin-tagged DNA or primer, or an antigen-tagged DNA or primer is fixed in each capillary, whereby the DNA sample or primer is fixed in the capillary by utilizing biotin-avidin bonding or antigen antibody reaction.

Still another aspect (constitution 6) of the present invention is characterized by an electrophoresis analysis apparatus comprising a DNA sample preparation apparatus of constitution 5, an electrophoresis analyzer and at least two analyzing capillaries having a sample-introducing portion at the end in which the reaction products produced in each capillary of the DNA sample preparation apparatus of constitution 5 are introduced into an analyzing capillary and analyzed by electrophoresis. The analysis apparatus is characterized in that the analyzing capillaries are filled with a gel or a sol, that the disposition of the capillaries is substantially the same as that of the sample-introducing portions at the ends of the analyzing capillaries, whereby the reaction products are introduced into the analyzing capillary and analyzed by electrophoresis, and that the analysis apparatus is equipped with a means for introducing the reaction products into the sample-introducing portion at the end of the analyzing capillary.

Still another aspect (constitution 7) of the present invention is characterized by a DNA sample preparation apparatus comprising a base plate having a plurality of first grooves for fixing two or more kinds of DNA samples or primers to the inner surfaces of the grooves, respectively, and a second groove filled with a reaction solution and communicating with the first grooves, wherein said reaction solution is introduced into the first grooves to be reacted with the two or more kinds of the DNA samples or primers independently at the same time.

Still another aspect (constitution 8) of the present invention is characterized by an electrophoresis analysis apparatus comprising a DNA sample preparation apparatus of constitution 7, an electrophoresis analyzer and at least two analyzing capillaries having a sample-introducing portion at the end in which the reaction products produced in each first groove of the DNA sample preparation apparatus of constitution 7 are introduced into an analyzing capillary and analyzed by electrophoresis. The analysis apparatus is characterized in that the analyzing capillaries are packed with a gel or a sol, that a portion into which the analyzing capillary can be inserted is formed at the end of each first groove, and that through this portion, the reaction products are introduced into the sample-introducing portion at the end of the analyzing capillary.

Still another aspect (constitution 9) of the present invention is characterized by a DNA sample preparation apparatus comprising a reaction solution vessel capable of accommodating a reaction solution and a plurality of reaction portions where the reactions of the reaction solution fed from the reaction solution vessel with each of a plurality of samples are independently carried out; and an electrophoresis analysis apparatus comprising a DNA sample preparation apparatus of constitution 9, an electrophoresis analyzer and at least two analyzing capillaries in which the reaction products produced in each reaction portion are introduced into an analyzing capillary and analyzed by electrophoresis. The analysis apparatus is characterized in that the analyzing capillaries are filled with a gel or a sol.

According to the present invention, as many as 100 samples can be subjected to sequencing reactions or fragment analysis reactions by using reagents conventionally used for reacting only two or three samples. Furthermore, as the amount of the reagents handled, a $\mu l$ order amount, a conventional amount is sufficient, so that not only saving but also easy handling of the reagents are possible.

BRIEF DESCRIPTION OF THE DRAWINGS

FIG. 2 shows a A–A' cross-sectional view illustrating the combination of a capillaries array analyzing portion and the DNA sample preparation apparatus in the first embodiment of the present invention, and a partially enlarged cross-sectional view illustrating an electric field applying portion.

FIG. 5A is a diagram illustrating the introduction of sample DNA's into capillary tubes which shows the third embodiment of the present invention utilizing the capillary tubes as reaction vessels.

FIG. 5B is a diagram illustrating the introduction of a reaction solution into the capillary tubes in the third embodiment of the present invention.

FIG. 5C is a diagram illustrating an operation of transferring samples to an analyzing capillary array in the third embodiment of the present invention.

FIG. 5D shows a base plate 22 having grooves in which capillaries 18 are used for holding a sample or reaction products 23. The reaction products are brought into contact with the sample introducing end of an analyzing capillary tube 21, in accordance with the third embodiment of the present invention.

DESCRIPTION OF THE PREFERRED EMBODIMENTS

The present invention is explained in further detail with the following embodiments with reference to the drawings.
First Embodiment In the first embodiment, template DNA's are fixed to a filter or the like and two or more kinds of samples are prepared at the same time. The first embodiment is explained below with reference to FIG. 1A, FIG. 1B, FIG. 2 and FIG. 3.

Figure 1A:
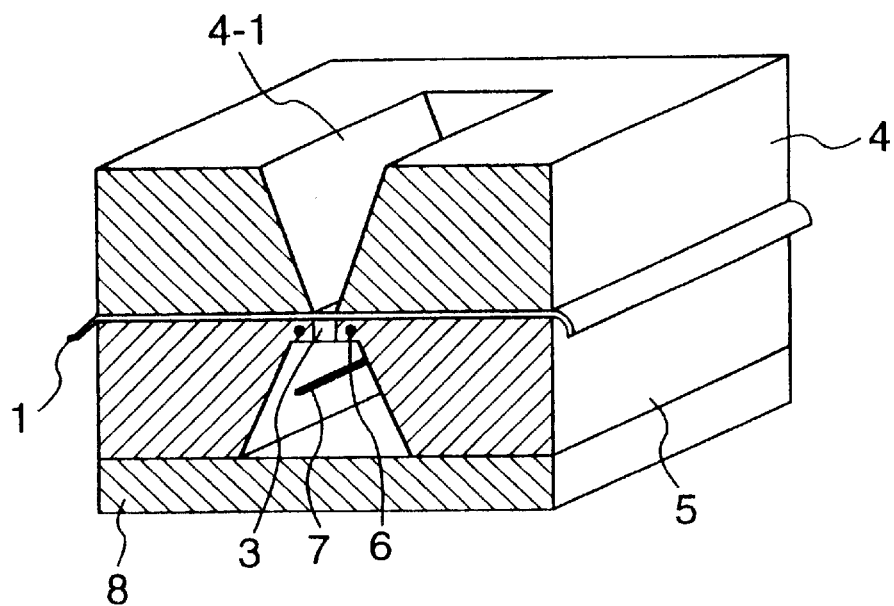
FIG. 1A is a perspective view including a section of a DNA sample preparation apparatus having a groove type reaction vessel in the first embodiment using a filter of the present invention.
Figure 1B:
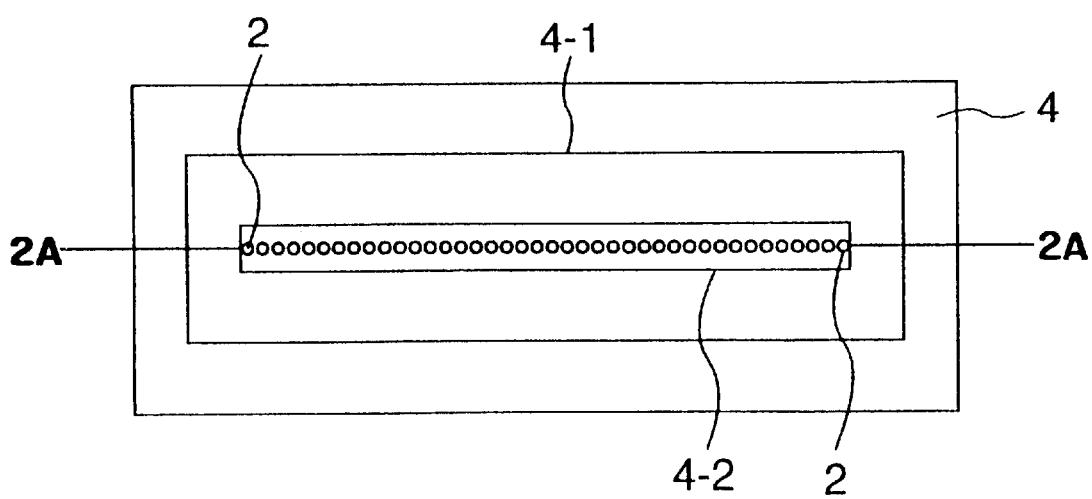
FIG. 1B is a plan view of the DNA sample preparation apparatus having a groove type reaction vessel in the first embodiment of the present invention.
Figure 3:
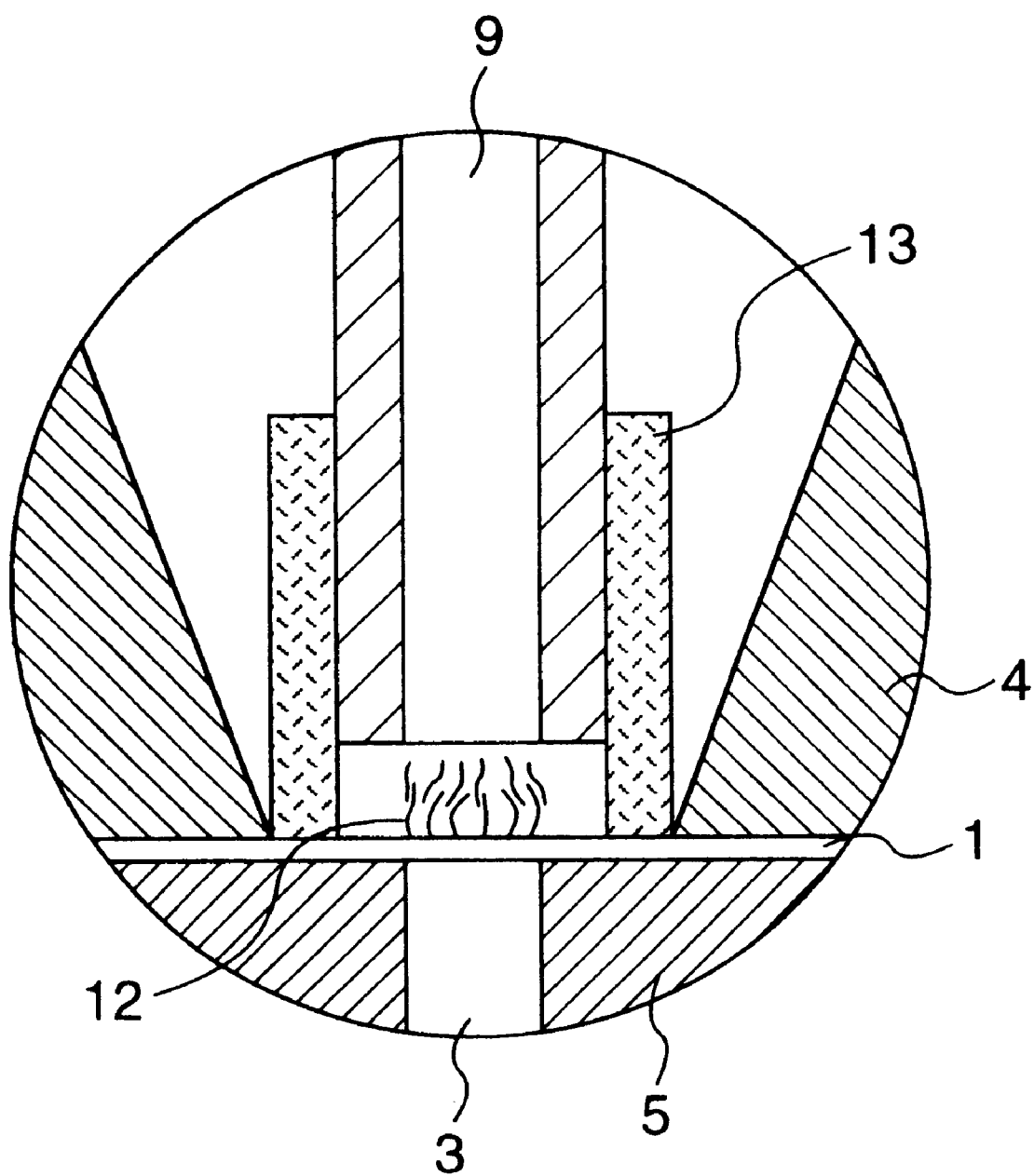
FIG. 3 is a partially enlarged cross-sectional view showing a modification of the electric field applying portion in the first embodiment of the present invention.

FIG. 1A and FIG. 1B are a section-including perspective view and a plan view, respectively, of a DNA sample preparation apparatus having a groove type reaction vessel (hereinafter referred to also as "reaction vessel") in the first embodiment using a filter. FIG. 2 shows a cross-sectional view illustrating the combination of a capillary array analyzing portion and the DNA sample preparation apparatus, and a partially enlarged cross-sectional view illustrating an electric field applying portion. FIG. 3 is a partially enlarged cross-sectional view showing a modification of the electric field applying portion.

First, an outline of the structure of the DNA sample preparation apparatus is explained below. The DNA sample preparation apparatus comprises an upper filter holder 4 having an upper open area (4-1 in FIG. 1-B) and a lower open area (4-2 in FIG. 1-B); a lower filter holder 5 having a plurality of small holes 3 (3-1, 3-2, ~, 3-N in FIG. 2) arranged in a line in the upper part and an open area in the lower part; a filter membrane 1 located between the upper filter holder 4 and the lower filter holder 5; and a lower cover 8 blocking up the open area in the lower part of the lower filter holder 5. The area of the lower open area 4-2 is sufficiently smaller than that of the upper open area 4-1, and a groove type reaction vessel having the filter membrane 1 in the bottom is formed by the upper open area 4-1, the lower open area 4-2 and the filter membrane 1.

In the lower part (within the lower open area 4-2) of the reaction vessel, avidin spots 2 for sample holding are formed by arranging spots of avidin in a line at positions corresponding to the small holes 3, respectively. As shown in FIG. 2, one end of a capillary electrophoresis tube 9 is located in the lower region of the reaction vessel at a position corresponding to each small hole 3 and avidin spot 2, and an electrode (a + electrode in FIG. 2) is located at the other end of the capillary electrophoresis tube 9, or the other ends of the capillary electrophoresis tubes 9 are located in an electrolysis solution vessel equipped with a + electrode.

A heater 6 is located along the plurality of the small holes 3 made in the filter holder 5, whereby the temperature of the groove type reaction vessel is controlled at a definite temperature by a temperature-controlling circuit (not shown). A buffer solution is introduced into a space formed by the open area in the lower part of the lower filter holder 5 and the lower cover 8 blocking up this open area, through the buffer solution inlet 10 of the lower cover 8 and discharged through its buffer solution outlet 11. Electrodes 7 (− electrodes in FIG. 2) are arranged in a line in the buffer solution.

There is a groove type reaction vessel having in the bottom a filter 1 having spots of avidin arranged thereon in a line. The pitch of the spots 2 is 0.5 mm. The spot size is 0.3 mm. As sample DNA's, those obtained by amplification by PCR are used. In this case, one of the primers is labelled with biotin. The filter is mounted on a perforated panel (the lower filter holder 5) and sucked from under the perforated panel. The suction is carried out by introducing a buffer solution through the buffer solution inlet 10 and discharging the buffer solution through the buffer solution outlet 11. The positions of the small holes 3 correspond to those of the avidin spots 2. A solution on the filter (a solution in the reaction vessel) is discharged through the avidin spots 2. When a biotin-labelled substance is present in the solution in the reaction vessel, it is captured by the avidin spot 2.

In detail, each DNA is amplified by PCR with a biotin-labelled primer to obtain a biotin-labelled DNA template. This product is held in a capillary tube with an inner diameter of 0.2 mm to 0.3 mm, and the end of the capillary is placed close to the avidin spot, and the product is provided from the capillary by sucking the template solution from the hole of the lower panel through the filter to be captured by the avidin. It is also possible to hold a plurality of samples in a large number of capillaries, respectively, and supply them on the plurality of spots to capture the samples, respectively. In this case, the disposition of the capillaries holding the samples is made the same as that of the avidin spots. A buffer solution is supplied on the filter and sucked together with the samples, which makes sheathflow and is effective to prevent the mixing of samples during sample capture at the spots. Thus, DNA's as templates can be fixed and arranged in a line at 0.5-mm intervals on the filter in the lower part of the groove. In the case shown in FIG. 1A and FIG. 1B, the length of the groove type reaction vessel having the filter in the bottom is 50 mm, the width of the groove 0.3 mm and the number of the spots 96.

The polymerase reactions are carried out in the groove type reaction vessel by adding about 10 $\mu$l of a reaction solution containing a fluoro-phore labelled primer, DNA polymerase, complementary chain synthesis substrates and the like. In the case of sequencing reaction, the reaction is carried out as sequencing reaction by using each of four kinds of terminators corresponding to four kinds of bases, respectively. That is, A reaction, C reaction, G reaction and T reaction are carried out using four groove type reaction vessels. On the other hand, when a so-called terminator method using fluorophore labelled dideoxy nucleotides is employed, sequencing can be carried out in one reaction vessel. This is because the sequencing reaction is carried out by one reaction by adding a mixture of four kinds of terminators (dideoxy nucleotides) labelled with different fluorophores to template DNA.

As shown in FIG. 2, each product has been hybridized with the template DNA fixed on the filter. The partially enlarged view in FIG. 2 shows the vicinity of the small hole 3-2, and numeral 12 shows the DNA produced by the reaction and the DNA fixed to the filter. The reaction vessel is washed with a buffer solution to remove the reagents, namely, the primer, reaction substrates (dNTP; deoxy nucleotide triphosphate and dd-NTP; dideoxy nucleotide triphosphate), etc. For injecting the reaction products into the capillaries, the sample-injecting end of each capillary of an analyzing capillary array 9 is placed close to the spot 2 holding the sample and a solution of formamide in ion-exchanged water is added to the vessel. The sample-holding portion is heated to 70° C. or higher with a heater 6 controlled by a temperature-controlling circuit, and an electric field is applied to the + electrode and the − electrode, whereby the DNA sample (reaction products) is introduced into a capillary electrophoresis portion 9. The components of the DNA sample are separated by subsequent electrophoresis and detected by fluorescence. In the case of the terminator labeling, it is sufficient that the introduction is carried out once. In the case of the primer labeling, the introduction for 5 seconds is repeated 4 times for the 4 terminal bases.

Usually, an electric field is produced by applying a voltage between an electrode on the side reverse to the filter surface holding DNA, i.e., the sucking hole sides and the capillary's end on the measuring portion sides, whereby samples are introduced into analyzing capillaries. The following is also possible: such a ring electrode 13 as is shown in FIG. 3 is provided outside each analyzing capillary and slided to be brought into contact with the filter surface, and an electric field is produced between the ring electrode 13 and the capillary 9. Of course, the following is also possible: a metal plate having holes for passing capillaries therethrough is brought into close contact with a filter, and sample-holding portions are allowed to coincide with the holes in position, after which the capillaries are inserted into the holes, and samples are introduced into the capillaries by applying an electric field between the metal plate and the capillaries. In the above explanation, the small holes 3 are arranged in a line, though needless to say, they may be arranged in a two-dimensional manner.

Second Embodiment

Figure 4A:
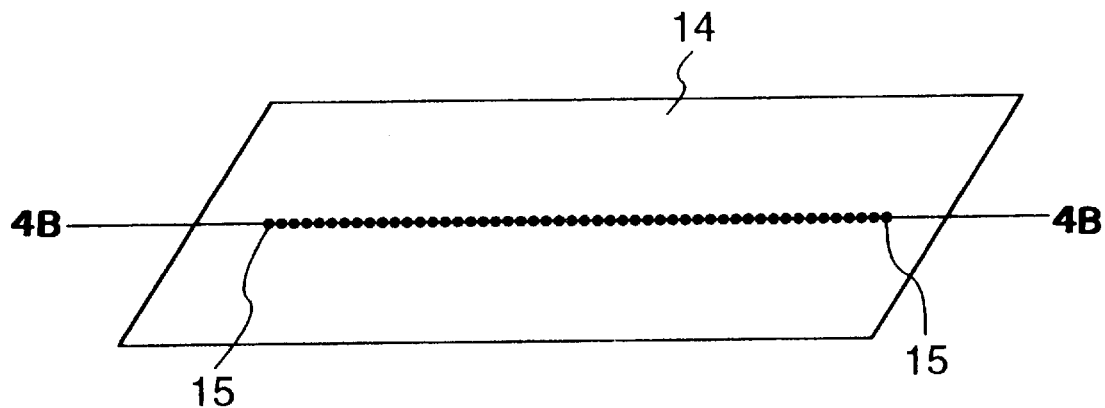
FIG. 4A is a plan view of a sheet having DNA-holding small holes which shows the second embodiment of the present invention using as reaction vessels the small holes made in plastic sheet.
Figure 4B:
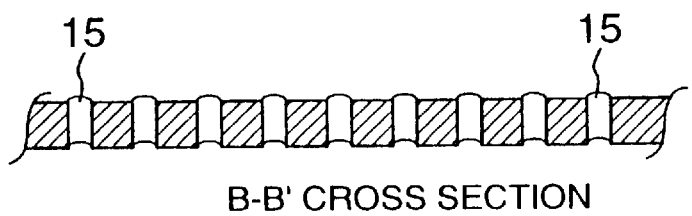
FIG. 4B is a partially enlarged B–B' cross-sectional view of the sheet having the small holes of the second embodiment of the present invention.
Figure 4C:
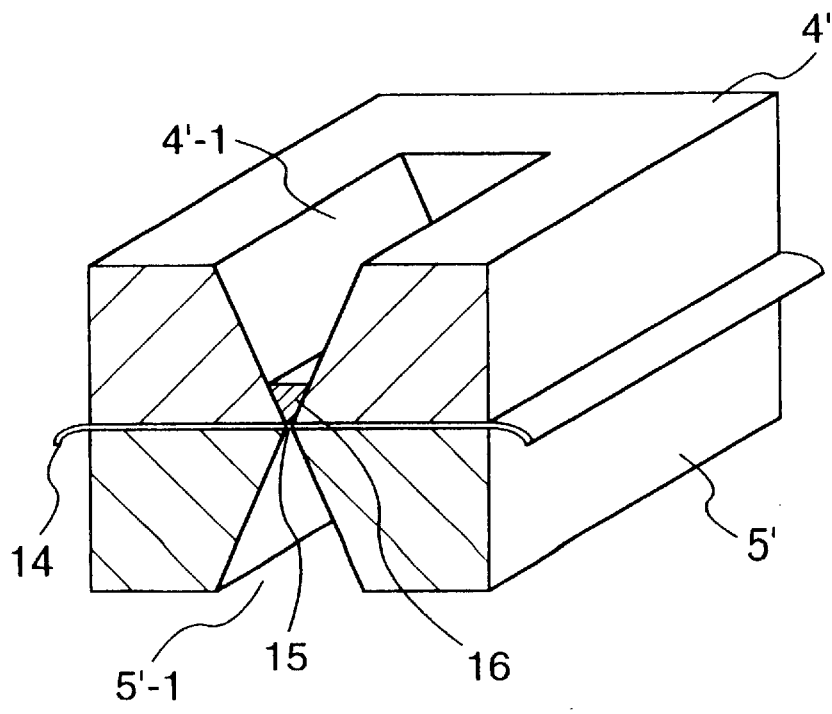
FIG. 4C is a perspective view including a section showing the combination of the sheet having the small holes and a reaction solution feeding means in the second embodiment of the present invention.

In the second embodiment, reactions are carried out in small holes arranged in a line. FIG. 4A is a plan view of a sheet having DNA-holding small holes which shows the second embodiment of the present invention using as reaction vessels the small holes made in plastic sheet. FIG. 4B is a partially enlarged cross-sectional view of the sheet having the small holes of the second embodiment of the present invention. FIG. 4C is a perspective view including a section showing the combination of the sheet having the small holes and a reaction solution feeding means in the second embodiment of the present invention. As shown in FIG. 4A, there is prepared a sheet having small holes 14 which is composed of a plastic sheet of 0.5 to 1 mm thickness having small holes (DNA holding small holes 15) with a diameter of 0.2 mm aligned thereon. Streptoavidin is immobilized inside the small holes 15. It is also possible to pack the small holes 15 with a porous material and immobilize streptoavidin in the porous material. The small holes 15 are arranged in a line at 1-mm intervals in a number of 100. Although the small holes may, of course, be arranged in a two-directional manner, an explanation is made here by taking the case of arranging the small holes in a line. When fluorophore labelled primers of 4 colors, respectively, are used, there is used an assembly obtained by placing such plastic sheets in a number of 4 one upon another.

As in the first embodiment, a DNA sample labelled with biotin is introduced into each small hole 15 and captured by the avidin immobilized on the wall of the small hole. After removing the solvent, the four sheets are separated and as shown in FIG. 4C, each sheet is sandwiched between an upper sheet holder 4' having a tapered open area 4'-1 and a lower sheet holder 5' having a tapered open area 5'-1. Thus, each sheet is exposed between the long and narrow openings of the upper sheet holder 4' and the lower sheet holder 5', respectively. The tapered open area 4'-1 of the upper sheet holder 4' serves as a reaction solution vessel into which a reaction solution 16 containing a primer and an enzyme is introduced. Since the reaction solution vessel is tapered, the reaction solution is collected in the lower part of the vessel. The width of the above-mentioned long and narrow opening is 0.2 mm and its length 100 mm.

The reaction solution intrudes into each small hole 15 and sequencing reaction proceeds. After completion of the reaction, the solvent is removed, followed by washing. The four sheets are placed one upon another so that their small holes coinside with one another in position, and a solution containing formamide is added. The end of each capillary is located so as to coincide in position with the small hole of the sheet. While heating the sheet holders 4' and 5' with a heater (not shown) controlled by a temperature controlling circuit in the same manner as in the first embodiment, the released samples are introduced into the capillaries by applying an electric field. Needless to say, the introduction of the samples by the application of an electric field may be carried out by employing the method shown in FIG. 3. Although the sheet having the holes is used here, the following is also possible: capillaries are arranged at a definite pitch in a one-or two-dimensional manner, united in a body with a thermoplastic plastic or glass and sliced in the direction perpendicular to the capillary axis, and the thus obtained holes are used as small holes.

Third Embodiment

In the third embodiment, capillary tubes are used as reaction vessels. FIG. 5A is a schematic view illustrating the introduction of sample DNA's into capillary tubes which shows the third embodiment of the present invention utilizing the capillary tubes as reaction vessels. FIG. 5B is a schematic view illustrating the introduction of a reaction solution into the capillary tubes in the third embodiment of the present invention. FIG. 5C is a schematic view illustrating an operation of transferring samples to an analyzing capillaries array in the third embodiment of the present invention. Although commercial quartz tubes were used as reaction tubes made of capillary 18, plastic tubes and the like may also be used. For increasing the reaction surface area, tubes with an inside diameter of 0.05 mm and a length of as long as 50 mm were used here, and streptoavidin was immobilized on the inner surfaces of the capillaries. As shown in FIG. 5A, 100 reaction tubes made of capillary (a bunch of capillaries) 18 are tied up in a bundle at one end of the bunch to be made attachable to the end of a microinjector 17. The opposite end of each reaction tube made of capillary 18 is put in a vessel (a sample reservoir) 19 containing template DNA, and the template DNA is introduced into the reaction tube made of capillary 18, by suction. The template DNA is fixed to the inner wall of the reaction tube made of capillary 18, by biotin-avidin bonding. Another method for introducing the templates comprises sucking each template into a short capillary tube, placing the short capillary tubes side by side in a groove, and introducing the templates into the above-mentioned bunch of the capillaries by suction.

After removing the solvent, a reaction solution is fed to each capillary by feeding the reaction solution to the injector 17 or sucking the reaction solution from a vessel 20 (a reaction solution reservoir or a reaction solution vessel) by means of the injector 17, and the reaction is carried out. After completion of the reaction, the solution is removed and the capillary 18 is filled with a solution containing formamide. Then, as shown in FIG. 5C, the end of the capillary 18 holding the reaction products 23 on the inner surface is brought into contact with the sample-introducing end of an analyzing capillary tube 21 (a + electrode). The capillary 18 holding the sample is heated and the sample is introduced into the analyzing capillary tube 21 by applying an electric field by using the shaft of the injector as the other electrode (a − electrode). For carrying out the above procedure smoothly, there was used a base plate 22 having grooves in which the capillaries 18 used for the sample holding (the reaction) and the analyzing capillaries were arranged and fixed at the same pitch (0.4 mm pitch in the present embodiment) so that the ends of the former might face with those of the latter, respectively. The sample introduced into each analyzing capillary 19 is separated and then detected in the same manner as in the above-mentioned first and second embodiments.

Fourth Embodiment

Figure 6A:
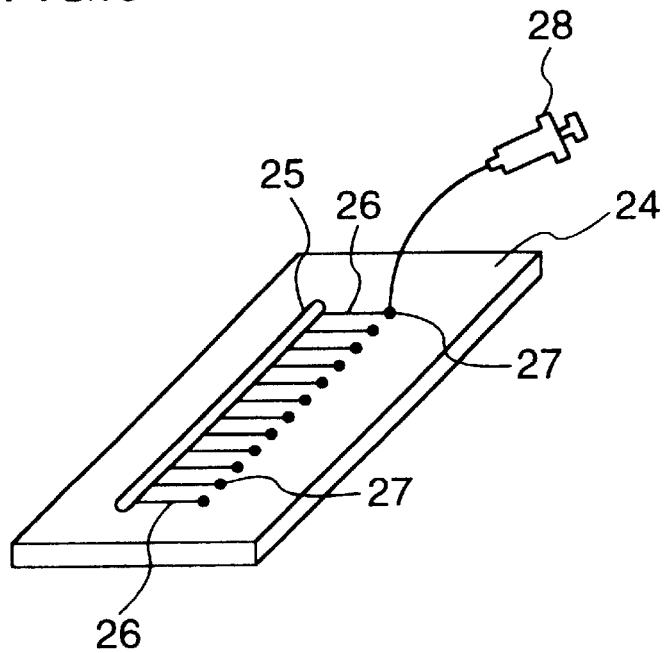
FIG. 6A is a perspective view of a base plate having a reaction solution vessel, reaction portions made of groove and capillary combining portions in the fourth embodiment of the present invention, which are formed by microfabrication.
Figure 6B:
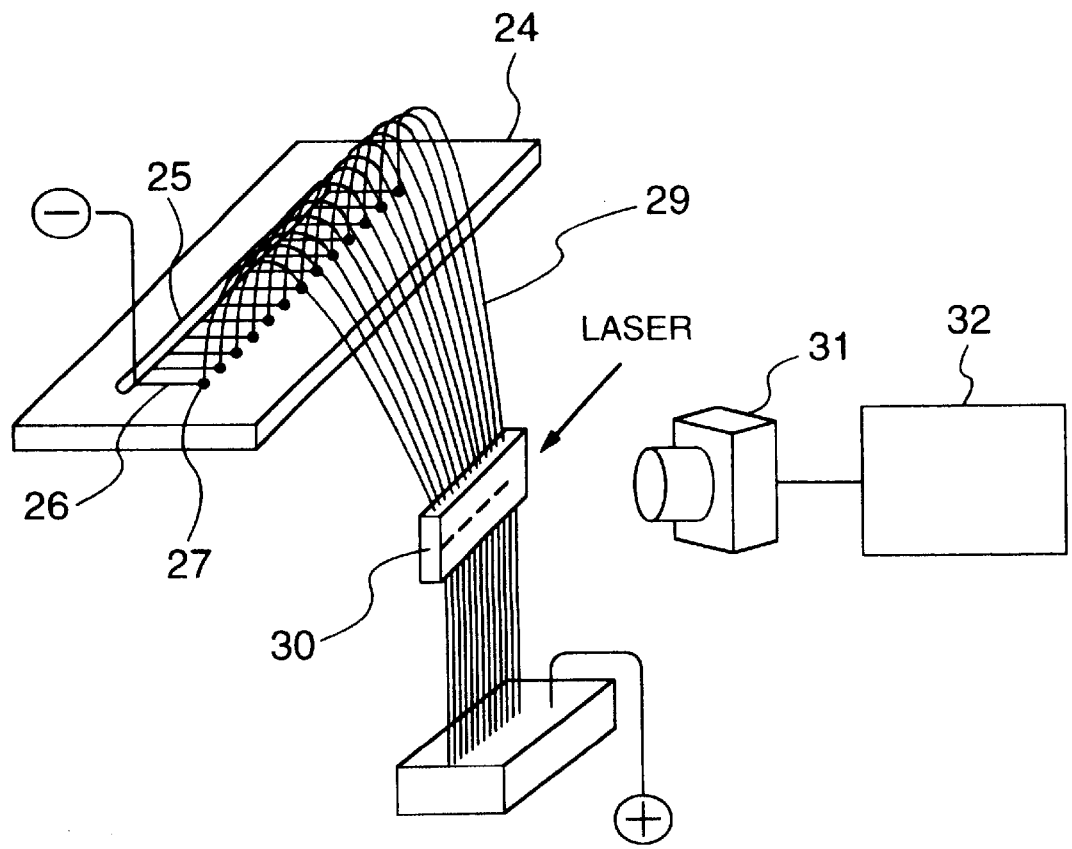
FIG. 6B is a perspective view illustrating the combination of the base plate and a capillary array electrophoresis apparatus in the fourth embodiment of the present invention.

In the fourth embodiment, there are used reaction vessels capable of also serving as sample-introducing portions, which are formed by microfabrication. FIG. 6A is a perspective view of a base plate having a reaction solution vessel, reaction portions made of groove, and capillary combining portions in the fourth embodiment of the present invention which is produced by microfabrication. FIG. 6B is a perspective view illustrating the combination of the base plate and a capillary array electrophoresis apparatus in the fourth embodiment of the present invention. A reaction vessel for capillary is preferably small-sized one in which a necessary amount of a sample is reacted and the whole reaction products are introduced into an analyzing portion if possible. However, less than 1 µl of reagents for reaction cannot be handled except the case where ink jet or the like is employed. Therefore, it is convenient to feed a µl-order amount of reagents to one portion and divide and deliver them to fine reaction vessels. The reaction products are introduced into capillary analysis portions or well portions for slab gel electrophoresis, which are spatially away from one another. Accordingly, it is advantageous for handling that portions for taking out the products are spatially away from one another. Such a disposition was realized by the use of the capillary tubes in the third embodiment, while it was realized by the use of the grooves formed by microfabrication, in the fourth embodiment.

FIG. 6A and FIG. 6B show the constitution of the present embodiment. As shown in FIG. 6A, a reaction solution vessel 25, reaction portions made of groove 26, and capillary combining portions 27 are formed in a base plate 24 (e.g. a silicon base plate or a glass base plate) by microfabrication. One end of each of the reaction portions made of groove 26 communicates with the reaction solution vessel 25, and the capillary combining portion 27 is formed at the other end. In the case shown in FIG. 6A, the reaction portions made of groove 26 are located only on one side of the reaction solution vessel, though needless to say, they may be located on both sides of the reaction solution vessel 25. The reaction solution vessel 25 is a vessel into which a reaction solution is fed. The reaction portions made of groove 26 are portions where reactions are carried out. For example, such grooves as shown in FIG. 6A are cut in a glass plate such as a slide glass and covered with a plastic film or the like. There is carried out a treatment for immobilizing avidin in the grooves used as the reaction portions made of groove 26.

For example, the dimensions of the reaction solution vessel 25 are as follows: width 0.5 mm, depth 0.2 mm, length 20 mm. The dimensions of the reaction portion made of groove 26 are as follows: width 0.2 mm, depth 0.2 mm, length 10 mm. The dimensions of the capillary combining portion 27 are as follows: bore 0.4 mm, depth 0.2 mm.

DNA is dropped in a hole (a hollow) 27 formed at the end of each groove used as the reaction portion made of groove 26, by means of a sample injector 28 having a thin tube connected thereto, and introduced into the groove 26 by capillarity. The template DNA has been previously labelled with biotin and is fixed in the groove 26. The solution containing the excess DNA is removed, after which 10 µl of a reaction solution is fed to the groove used as the reaction solution vessel 25 and injected into the grooves used as the reaction portions made of groove 26 by applying a pressure (the pressure is obtained, for example, by applying a force on the aforesaid cover such as a plastic film to deform the cover). The reaction solution contains DNA polymerase, a primer, dNTP's as reaction substrates, etc., and reacts with the template DNA fixed on the wall of each groove 26, to produce products. Even after removal of the reaction solution and washing after the completion of the reaction, the products remains in the groove 26 while they are still hybridized with the template DNA. A formamide solution is fed to the grooves 26 and the base plate is heated. An electrode (a − electrode) is placed in the groove used as the reaction solution vessel 25, and the sample-introducing end of each capillary analyzing tube [a capillary analyzing portion (one end thereof is connected to a light irradiation portion 30)] 29 is brought into contact with the hole formed at the end of the groove used as the reaction portion made of groove 26. The sample is introduced into the capillary analyzing portion 29 by applying an electric field (FIG. 6B). The sample introduced into the capillary analyzing portion 29 is separated and then detected in the same manner as in the above-mentioned first, second and third embodiments. In FIG. 6B, numeral 31 shows a fluorescence detector and numeral 32 a data processing unit. The fourth embodiment is summarized below with reference to FIG. 6A and FIG. 6B. In a base plate 24, there are formed a reaction solution vessel 25 to which a reaction solution is fed, reaction portions made of groove 26 in which avidin is immobilized, and capillary combining portions 27. DNA is dropped in each capillary combining portion 27 by means of a sample injector 28 and introduced into the groove 26. Biotin-labelled template DNA is fixed in the groove 26, after which the solution containing the excess DNA is removed. A reaction solution containing DNA polymerase, a primer, dNTP's as reaction substrates, etc. is fed to the reaction solution vessel and introduced into the groove used as reaction portion made of groove 26, to be reacted with the template DNA. After removing the reaction solution, followed by washing, a formamide solution is fed to the grooves 26 and the base plate is heated. An electrode is placed in the reaction solution vessel 25, and the sample-introducing end of each capillary analyzing portion 29 is brought into contact with the capillary combining portion 27. The sample is introduced into the capillary analyzing portion 29 by applying an electric field, separated by electrophoresis and then detected. As a result, a large number of samples can be reacted by handling reagents in a μl-order amount, and there can be realized a DNA sample preparation apparatus for capillary electrophoresis which permits large-scale base sequence analysis.

What is claimed is:

1. An electrophoresis analysis apparatus comprising:
   (a) a DNA sample preparation apparatus comprising:
      a filter membrane divided into different sections, having spots of avidin arranged thereon, in the different sections, respectively; and
      a holder holding the filter membrane at an under part thereof and having an open area,
      wherein a plurality of biotin-tagged DNA samples are fixed at the different sections by biotin-avidin bonding, respectively; and
      wherein a reaction solution is introduced into a space formed by said filter membrane and said open area and reactions including DNA complementary chain synthesis are carried out at the same time, independently, in said different sections, in the space formed by said filter membrane and said open area;
   (b) a plurality of analyzing capillaries each having a sample-introducing portion at an end thereof; and
   (c) a metal plate electrode for introducing said reaction products into the sample-introducing portions of said analyzing capillaries, wherein said metal plate electrode contacts with the filter membrane and has holes for passing through the analyzing capillaries therethrough, respectively, and
   wherein positions of the holes of the metal plate electrode coincide with positions of the spots of avidin,
   wherein the reaction products produced in said different sections of DNA sample preparation apparatus are introduced into said analyzing capillaries, respectively and analyzed by electrophoresis.

2. An electrophoresis analysis apparatus comprising:
   (a) a DNA sample preparation apparatus comprising;
      an upper holder having an upper open area, and a lower open area having an area smaller than an area of the upper open area;
      a lower holder having a plurality of small holes arranged in an upper part; and
      a filter membrane having a plurality of spots of avidin arranged thereon, separately,
      wherein the filter membrane is located between the upper hold and the lower holder, such that positions of the spots of avidin correspond to positions of the small holes of the lower holder respectively;
      wherein a plurality of biotin-tagged samples are captured at the spots of avidin, respectively, by biotin-avidin bonding; and
      wherein a reaction vessel having a tapered cross section is formed by the upper open area of the upper holder, the lower open area of the upper holder and the filter membrane, and, to obtain DNA fragments for analyzing DNA samples, DNA polymerase reactions are carried out after adding a reaction solution containing a fluorophore labeled primer, DNA polymerase, and complementary chain synthesis substrates into the reaction vessel;
   (b) a plurality of analyzing capillaries each having a sample-introducing portion at the end; and
   (c) a metal plate electrode for introducing said reaction products into the sample-introducing portions of the analyzing capillaries, wherein said metal plate electrode contacts with the filter membrane and has holes for passing through the analyzing capillaries therethrough, respectively, and wherein positions of the holes of the metal plate electrode coincide with positions of the spots of avidin,
   wherein the reaction products produced in the sections of the DNA sample preparation apparatus are introduced into the analyzing capillaries, respectively and analyzed by electrophoresis.

* * * * *